United States Patent [19]

Vanlerberghe et al.

[11] 4,303,639
[45] Dec. 1, 1981

[54] 1,2-ALKANEDIOL DERIVATIVES IN COSMETIC COMPOSITIONS AS AN EXCIPIENT THEREFOR

[75] Inventors: Guy Vanlerberghe, Montjay-La-Tour; Henri Sebag, Paris, both of France

[73] Assignee: Societe Anonyme dite: l'Oreal, Paris, France

[21] Appl. No.: 760,921

[22] Filed: Jan. 21, 1977

Related U.S. Application Data

[63] Continuation of Ser. No. 602,963, Aug. 8, 1975, abandoned.

[30] Foreign Application Priority Data

Aug. 12, 1974 [LU] Luxembourg .................... 70718

[51] Int. Cl.³ .............. A61K 7/021; A61K 7/025; A61K 7/031; A61K 7/032
[52] U.S. Cl. .................. 424/63; 260/410.6; 424/59; 424/64; 424/65; 424/365; 568/678; 424/45
[58] Field of Search .................. 424/63, 64, 65, 358, 424/365, 172; 260/410.6, 484 R, 614 R; 568/675, 678

[56] References Cited

U.S. PATENT DOCUMENTS

| | | | |
|---|---|---|---|
| 1,917,256 | 7/1933 | Harris | 260/410.6 |
| 1,958,700 | 5/1934 | Harris | 260/410.6 |
| 2,109,842 | 3/1938 | Harris | 260/410.6 |
| 2,118,506 | 5/1938 | Graves | 260/410.6 X |
| 2,174,761 | 10/1939 | Schuette et al. | 260/458 |
| 2,213,477 | 9/1940 | Steindorff et al. | 260/613 |
| 2,628,187 | 2/1953 | Frohmader et al. | 424/83 X |
| 2,628,205 | 2/1953 | Shoemaker | 424/83 X |
| 3,196,079 | 7/1965 | Blaustein | 424/83 X |
| 3,215,599 | 11/1965 | Thau et al. | 424/83 |
| 3,651,102 | 3/1972 | Coopersmith | 260/410.6 |
| 3,914,407 | 10/1975 | Kalopissis et al. | 424/365 |

FOREIGN PATENT DOCUMENTS 2121175  8/1972  France .

*Primary Examiner*—Natalie Trousof
*Assistant Examiner*—Vera C. Clarke
*Attorney, Agent, or Firm*—Cushman, Darby & Cushman

[57] ABSTRACT

A 1,2-alkanediol derivative has the formula

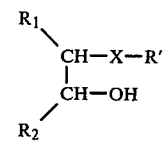

wherein X represents oxygen or

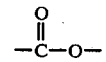

linked to R' through the free bond of the carbon atom of the carbonyloxy group, R' represents saturated alkyl having 5–21 carbon atoms or wherein X represents

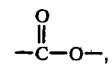

R' represents the hydrocarbon residue of lanolic acid, one of $R_1$ and $R_2$ represents linear alkyl having 8 to 16 carbon atoms and the other represents hydrogen, and mixtures of said derivative. The said derivative or mixtures thereof is employed as an excipient in cosmetic compositions.

22 Claims, No Drawings

1,2-ALKANEDIOL DERIVATIVES IN COSMETIC COMPOSITIONS AS AN EXCIPIENT THEREFOR

This is a continuation of application Ser. No. 602,963 filed Aug. 8, 1975 the entire specification of which is hereby incorporated by reference, now abandoned.

The present invention relates to derivatives of 1,2-alkanediol, as well as to their use in cosmetic compositions.

Heretofore, 1,2-alkanediols have been proposed for various uses, including principally, as an emollient in cosmetic compositions such as lotions, creams and lip rouges. Further 1,2-alkanediols have been described as synergistic agents in foam compositions such as shampoo or bath foam formulations. These alkanediols have also been described as intermediates for use in the preparation of nonionic surface active agents, the latter usefully being employed chiefly in shampoo compositions or in cosmetic emulsions.

It has now been found that certain ether and ester derivatives of 1,2-alkanediols which exhibit an appearance of an oil or a soft wax and have the capability of being easily spread onto living human skin can advantageously be employed in the preparation of cosmetic compositions.

The 1,2-alkanediol derivatives of the present invention are practically colorless and odorless and can be provided in the form of an oil, a semi-liquid compound or a wax, depending on the particular nature of the substituents found in the molecule thereof. These 1,2-alkendiol derivatives are also miscible with those oils and waxes conventionally employed in the preparation of cosmetic compositions and thereby permits their use, either alone or as mixtures, in cosmetic compositions such as skin treatment of protective compositions, makeup compositions or bath compositions.

The presence of these 1,2-alkanediol derivatives in such compositions impart thereto remarkable properties of unctuousness, ease of application, very good spreadability on the skin, without an oily or greasy feel or touch.

The present invention particularly relates to derivatives of 1,2-alkanediols as well as mixtures thereof, having the formula

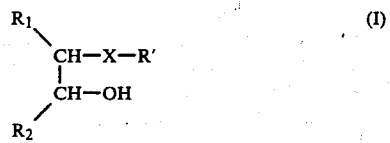

(I)

wherein X represents a member selected from the group consisting of oxygen and a carbonyloxy group of the formula

linked to R' group through the free valence bond of the carbon atom of said carbonyloxy group, R' represents saturated alkyl having 5-21 carbon atoms, or, in the case where X represents

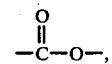

R' represents a mixture of the hydrocarbon residues of lanolic acid, one of $R_1$ and $R_2$ represents linear alkyl having 8-16 carbon atoms and the other represents hydrogen.

R' can represent principally the hydrocarbon residue of a R'—OH alcohol or a R'—COOH acid, the R'—OH alcohol being selected from the group consisting of 2-ethyl hexanol, octanol, decanol, dodecanol, tetradecanol, hexadecanol, 2-hexyl decanol, 2-octyl decanol, octyl octanol, isostearyl alcohol and 2-octyl dodecanol, and the R'—COOH acid being selected from the group consisting of 2-ethyl butyric acid, 2-ethyl hexanoic acid, octanoic acid, 3,5,5-trimethyl hexanoic acid, decanoic acid, dodecanoic acid, neo-tridecanoic acid, tetradecanoic acid, hexadecanoic acid, isopalmitic acid, isostearic acid, octadecanoic acid, eicosanoic acid and docosanoic acid, or even the hydrocarbon residue of lanolic acid.

Lanolic acid can be obtained by the hydrolysis of lanolin and it comprises a mixture of fatty acids including principally aliphatic acids, substituted or not, as well as hydroxylated acids. Up to 36 different fatty acids have been found in lanolic acid. A representative lanolic acid usefully employed in the present invention is one sold by Croda having a saponification index of 174 and an iodine index of 22.

Representative linear alkyls of $R_1$ or $R_2$ are selected from the group consisting of octyl, nonyl, decyl, undecyl, dodecyl, tridecyl, tetradecyl, pentadecyl and hexadecyl.

The present invention also relates to a process for preparing the 1,2-alkanediol derivatives defined above comprising reacting one or more alcohols or acids of the formula R'—X—H with one or more 1,2-epoxides of the formula

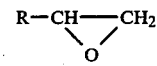

wherein R is a linear alkyl or mixture thereof, said alkyl having 8-16 carbon atoms.

When R'—X—H represents an alcohol, i.e. when X is oxygen, the reaction is carried out in the presence of an acid catalyst, such as a Lewis acid catalyst, for example, boron trifluoride, or in the presence of an alkaline catalyst, such as sodium methylate.

When R'—X—H represents an acid, i.e. when X represents

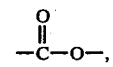

the reaction is carried out in the presence of a basic catalyst, such as sodium methylate or triethylamine.

The opening of the epoxide is not unequivocal, particularly in the case where boron trifluoride is used as the catalyst, so that the reaction leads generally to a mixture of isomers. The first of such isomers corresponds to one where $R_1=H$ and $R_2=R$; the second isomer corresponds to one where $R_1=R$ and $R_2=H$.

The production of the two isomers is not prejudicial to the ultimate properties of the 1,2-alkanediol derivative of formula I and thus there is no real need to separate them.

The R'OH alcohols usefully employed in the above process can be, for example, 2-ethyl hexanol, octanol, decanol, dodecanol, tetradecanol, hexadecanol, 2-hexyl decanol, 2-octyl decanol, octyl-octanol, isostearyl alcohol and 2-octyl dodecanol.

The R'COOH acids usefully employed in the process described above are principally 2-ethyl butyric acid, 2-ethyl hexanoic acid, octanoic acid, 3,5,5-trimethyl hexanoic acid, decanoic acid, dodecanoic acid, neotridecanoic acid, tetradecanoic acid, hexadecanoic acid, isopalmitic acid, isostearic acid, octadecanoic acid, eicosanoic acid, docosanoic acid and lanolic acid.

By "neo-tridecanoic acid" is meant a mixture of isomers having branched chains of tridecanoic acid.

The epoxides of formula II usefully employed in the process of the present invention are principally the oxides of decene, undecene, dodecene, tridecene, tetradecene, pentadecene, hexadecene, heptadecene and octadecene.

Certain of these epoxides are sold in the form of mixtures which can also be used in the present process.

The reaction of the R'COOH acid or the R'OH alcohol with the epoxide compound of formula II is effected without a solvent, at a temperature ranging from 60° to 150° C.

Stoichiometric amounts of the reactants are employed when R'—XH represents a carboxylic acid whereas when R'—XH represents an alcohol, a 100–500% molar excess of the alcohol relative to the epoxide of formula II is employed.

The molar proportion of catalyst employed relative to the epoxide ranges from about 0.2 to 5 percent.

Acidic or basic impurities are removed from the product of the reaction by washing the same with hot water at a temperature between 50° and 95° C. after neutralization.

The products obtained in accordance with the process of this invention are dried and purified by heating the same under reduced pressure to remove excess reactants and the purification of these products can be completed by molecular distillation thereof.

The compounds of formula I can also be prepared by reacting an acid or alcohol of the formula R'—XH with a 1,2-alkanediol in accordance with conventional procedures. However, the compounds of formula I are preferably prepared from the epoxides of formula II.

The present invention also relates to a cosmetic excipient, comprising the derivative of formula I described above, or a mixture thereof for use in the preparation of cosmetic compositions.

The present invention particularly relates to the use in the preparation of cosmetic compositions, as an excipient therein, of the derivatives of 1,2-alkanediols obtained in accordance with one of the processes described above, and in accordance with the procedures set forth hereafter in Examples 1–12.

The present invention further relates to a cosmetic composition containing as an excipient therefor at least one derivative of formula I above.

The cosmetic compositions according to the present invention are principally those wherein the excipient is prepared in accordance with one of the processes described above and particularly to cosmetic compositions wherein the said excipient is prepared in accordance with Examples 1–12 given below.

The 1,2-alkanediol derivatives of the present invention can be used as excipients for the production of numerous cosmetic formulations including, without being limited thereto, milks, creams, emulsion for the application to the skin, various makeup products such as lip rouge and cheek rouge, blushes and foundations for the face, bath compositions and products for protection against solar rays.

The 1,2-alkanediol derivatives of the present invention are generally used in the cosmetic compositions in an amount which can vary to a large degree depending on the type of cosmetic formulation selected.

This amount ranges generally between 0.15 and 70%, and preferably between 0.2 and 50% by weight, relative to the total weight of the composition.

The said 1,2-alkanediol derivative can be used alone or in admixture with conventional natural or synthetic oils and waxes.

The cosmetic compositions of the invention can contain, in addition to the derivatives of formula I, conventionally employed active components or other excipients, such as surface active agents, dyes, perfumes, astringent agents, ultra-violet absorbing products, preservatives, water, alcohol and the like.

These compositions which can be prepared in accordance with conventional procedures can comprise lip rouges, deodorants, eyelid liner or shadow formulations, creams for the application to the face, hands and other parts of the human body including anti-solar creams, makeup remover creams, dye foundation creams, liquid dye foundation formulations, makeup remover milks, anti-solar milks or bath oils and the like.

The following non-limiting examples illustrate the invention. In these examples, R represents one of $R_1$ or $R_2$, the other representing hydrogen. Unless otherwise stated, all parts and percentages are by weight.

EXAMPLES OF PREPARATION

EXAMPLE 1

Preparation of a mixture of compounds of formula I wherein R represents alkyl radicals having from 9 to 12 carbon atoms, R' represents the hydrocarbon residue of isostearyl alcohol and X represent oxygen.

To 175 g (0.6 mole) of isostearyl alcohol, there is added 0.6 cc of a $BF_3.CH_3$—COOH complex containing 33% $BF_3$. The resulting mixture is heated to 75° C. and there are then added dropwise 64 g (0.3 mole) of a mixture of $C_{11}$ to $C_{14}$ fatty epoxides sold under the name Nedox 1114, while maintaining the temperature at 70°–75° C. At the end of the addition, the reaction mixture is heated to 80° C. for 1 hour.

The almost total disappearance of the epoxide introduced is then verified and to the reaction mixture, with agitation, there are added 200 cc of water at 95° C. containing 1 g of a 48% NaOH solution. The aqueous phase is drawn off after decantation and the remaining organic phase is washed twice with 200 cc of water at 95° C. The resulting product is dried by heating it under reduced pressure.

Excess alcohol is then distilled off by molecular distillation at 100° C. under 0.07 mm Hg. The product obtained is then distilled at 180° C. under $10^{-3}$ mm Hg, yielding a colorless-semi-crystallized product having an end melting point of +29° C. and an Index of Refraction at 30° C.=1.45428.

EXAMPLE 2

Preparation of a compound of general formula I wherein R represents tetradecyl, R' represents 2-ethyl hexyl and X represents oxygen.

To 130 g (1 mole) of 2-ethyl-hexanol-1, there is added 0.5 cc of a $BF_3$.acetic acid complex at a temperature of 70° C. To the resulting mixture there are added 122 g (0.22 mole) of 1,2-epoxy hexadecane over a period of 35 minutes, the temperature being maintained at 70°-80° C.

Then, by dosage the disappearance of the epoxide introduced is verified and to the reaction mass there are added with agitation 100 cc of water at 80° C. The aqueous phase is drawn off after decantation and the remaining organic phase is dried under a vacuum and then distilled, yielding, after the removal of the excess alcohol, a colorless oil having a boiling point=169°-170° C. under 0.05 mm Hg), an Index of Refraction at 30° C.=1.44823, and an end melting point=+2° C.

EXAMPLE 3

Preparation of a mixture of compounds of general formula I wherein R represents dodecyl and tetradecyl, R' represents 2-hexyl decyl and X represents oxygen.

To 152.4 g (0.6 mole) of 2-hexyl decanol, there is added 0.6 cc of a $BF_3.CH_3COOH$ complex (33% $BF_3$). The resulting mixture is heated to 75° C., after which there are added dropwise 73 g (0.3 mole) of a mixture of $C_{14}$ and $C_{16}$ fatty epoxides while maintaining the temperature at 75°±5° C. At the end of the addition, the reaction mixture is heated for 1 hour at 80° C. To the reaction mass there are then added, with agitation, 200 cc of water at 95° C. containing 1.4 g of a 48% NaOH solution. The aqueous phase is drawn off after decantation and the remaining organic phase is washed twice with 200 cc of water at 95° C. The resulting product is then dried by heating under reduced pressure and the excess alcohol is distilled off by molecular distillation at 100° C. under 0.1 mm Hg. The product obtained is then further purified by molecular distillation at 195° C., yielding a colorless oil having an end melting point near −10° C., a viscosity at 30° C.=0.48 poise and an Index of Refraction at 30° C.=1.45280.

EXAMPLE 4

Preparation of a mixture of compounds of general formula I wherein R represents alkyl radicals having from 9–12 carbon atoms, R' represents the hydrocarbon residue of 2-ethyl butyric acid and X represents

To 46.4 g (0.4 mole) of 2-ethyl butyric acid, there is added 0.81 g (0.008 mole) of triethylamine. The resulting mixture is then heated under a nitrogen atmosphere to 135° C. after which there are added dropwise over a period of 35 minutes 85.2 g (0.4 mole) of a mixture of $C_{11}$ to $C_{14}$ fatty epoxides sold under the name of Nedox 1114. After heating this reaction mixture for 2 hours at 135° C., the amount of the reaction, determined by the disappearance of the acid index is 96%.

There are then added to the reaction mass with agitation 130 cc of water at 80° C. containing 1.3 g of a 48% NaOH solution so as to neutralize the remaining acid. The aqueous phase is drawn off after decantation and the remaining organic phase is washed initially with 130 cc of water containing 0.3 cc HCl (d=1.19) so as to neutralize the triethylamine and then with 130 cc of water at 80° C. The reaction mass is then dried under reduced pressure. Unreacted reactants are removed by molecular distillation at 70° C. under $10^{-3}$ mm Hg, and the product thus obtained is distilled at 135° C., under the same pressure, yielding a slightly yellow liquid having an end melting point lower than −15° C., an Index of Refraction at 30° C.=1.44552 and a viscosity at 30° C.=0.25 poise.

EXAMPLE 5

Preparation of a mixture of compounds of general formula I wherein R represents alkyl radicals having from 13 to 16 carbon atoms, R' represents the hydrocarbon residue of 2-ethyl hexanoic acid and X represents

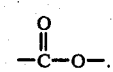

To 220 g (1.5 moles) of 2-ethyl hexanoic acid there are added 5.8 g of a solution of sodium methylate in methanol at 5.16 meq/g (0.03 mole). The resulting mixture is then heated to 70° C. under 15 mm Hg to extract the methanol. The temperature of the reaction mixture is then raised to 130° C. under a nitrogen atmosphere at which point there are added dropwise 378 g of a mixture of $C_{15}$ to $C_{18}$ fatty epoxides sold under the name Nedox 1518. After heating the resulting mixture for 6½ hours at 130° C., the amount of the reaction determined by acid index is 90%. Unreacted reactants are removed by distillation under 0.1 mm Hg, at a temperature of 135° C., then by molecular distillation under $10^{-3}$ mm Hg at 110° C. The product is then distilled by this process at 150° C., yielding a colorless and odorless oil having an end temperature of liquefaction of 2° C., an Index of Refraction at 30° C.=1.44884 and a viscosity at 30° C.=0.36 poise.

EXAMPLE 6

Preparation of a mixture of compounds of general formula I wherein R represents dodecyl and tetradecyl, R' represents the hydrocarbon residue of isostearic acid and X represents

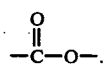

To 79.6 g (0.25 mole) of isostearic acid there is added 0.42 g (0.0075 mole) of sodium methylate. The resulting mixture is then heated under a nitrogen atmosphere to 130° C. at which point there are added dropwise 61 g (0.25 mole) of a mixture of $C_{14}$ and $C_{16}$ fatty epoxides over a 15 minute period. Subsequently, the resulting mixture is heated for 7 hours at 130° C. at which point the amount of the reaction, determined by acid index, is 96%.

To the reaction mass there are added initially 125 cc of water at 80°-90° C. containing 0.85 g of a 48% NaOH solution so as to neutralize the remaining acid and then 20 cc of isopropanol to facilitate decantation. The aqueous phase is withdrawn and the remaining organic phase is washed 3 times with 125 cc of hot water. The reaction mass is then dried by heating under a partial vacuum and the remaining unreacted reactants are removed by molecular distillation at 120° C. The product obtained is then purified by molecular distillation at 190° C. under 10⁻³ mm Hg, yielding a slightly yellow solid product having an end melting point of +45° C. and an Index of Refraction at 50° C.=1.44923.

EXAMPLE 7

Preparation of a mixture of compounds of general formula I wherein R represents alkyl radicals having 9 to 12 carbon atoms, R' represents the hydrocarbon residue of 3,5,5-trimethyl hexanoic acid and X represents

To 63.5 g of 3,5,5-trimethyl hexanoic acid there is added 0.8 g (0.008 mole) of triethylamine. The resulting mixture is heated under a nitrogen atmosphere to 135° C. There are then added dropwise over a period of 45 minutes, 85.2 g (0.4 mole) of a mixture of $C_{11}$ to $C_{14}$ fatty epoxides sold under the name Nedox 1114. After heating the reaction mixture for 3 hours at 135° C., the amount of the reaction, determined by acid index, is 96%. To the reaction mass there are added, with agitation, 150 cc of water at 80° C. containing 1.25 g of a 48% NaOH solution so as to neutralize the remaining acid. The aqueous phase is drawn off after decantation and the remaining organic phase is initially washed 3 times with 150 cc of hot water containing 0.3 cc of HCl (d=1.19) so as to neutralize the triethylamine and then it is washed with 150 cc of water. The remaining reactants are removed by heating under reduced pressure (0.1 mm Hg). The product is then purified by molecular distillation (135° C. under 10⁻³ mm Hg) yielding a colorless oil having an end melting point near −10° C., an Index of Refraction at 30° C.=1.44784 and a viscosity at 30° C.=0.36 poise.

EXAMPLE 8

Preparation of a mixture of compounds of general formula I wherein R represents dodecyl and tetradecyl, R' represents the hydrocarbon residue of 2-ethyl hexanoic acid and X represents

To 108 g (0.73 mole) of 2-ethyl hexanoic acid there are added 3 g of a solution of sodium methylate in methanol, 5.16 meq/g (0.014 mole). The resulting mixture is heated to 90° C. under 20 mm Hg to remove the methanol at which point the temperature is raised to 130° C. under a nitrogen atmosphere. There are then added dropwise over a period of 1½ hours, 176 g (0.72 mole) of a mixture of $C_{14}$ and $C_{16}$ fatty epoxides. After heating the reaction mixture for 7¼ hours at 130°±5° C., the amount of the reaction, determined by acid index, is 93%. The unreacted reactants are removed by molecular distillation at 100° C. The product obtained is purified by molecular distillation at 135° C. under 10⁻³ mm Hg, yielding a colorless and odorless oil having a melting temperature of −11° C., an Index of Refraction at 30° C.=1.44793 and a viscosity at 30° C.=0.33 poise.

EXAMPLE 9

Preparation of a mixture of compounds of general formula I wherein R represents alkyl radicals having from 13 to 16 carbon atoms, R' represents heptadecyl and X represents

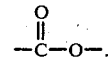

To 67.5 g (0.25 mole) of molten stearic acid there is added 0.5 g (0.005 mole) of triethylamine. The resulting mixture is heated to 135° C. under a nitrogen atmosphere at which point there are added dropwise over a period of 25 minutes, 63 g (0.25 mole) of a mixture of $C_{15}$ to $C_{18}$ fatty epoxides sold under the name Nedox 1518. After heating the reaction mixture for 3 hours at 135° C., the amount of reaction, determined by acid index, is 98%. To the molten reaction mass there are then added 200 cc of water at 95° C. containing 4 g of NaOH (1.2 meq/g) so as to neutralize the remaining acid. Subsequently 100 cc of isopropanol are added to facilitate decantation. The aqueous phase is separated and the remaining organic phase is washed initially with 200 cc of water at 95° C. containing 0.5 cc of concentrated HCl (d=1.19) and then with 200 cc of water at 95° C. The product is dried by heating under reduced pressure, yielding a white product solid at ambient temperature and having an end liquefaction point of 65° C.

EXAMPLE 10

Preparation of a mixture of compounds of general formula I wherein R represents $C_{10}H_{21}$, R' represents the hydrocarbon residue of lanolic acid and X represents

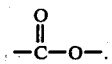

To 167 g (0.4 mole) of molten lanolic acid there are added 1.1 g of powdered sodium methylate (20 meq). The temperature of the resulting mixture is raised to 130° C. under a nitrogen atmosphere at which point there are added dropwise over a period of 30 minutes, 73.6 g (0.4 mole) of 1,2-epoxy dodecane. The temperature of the reaction mixture is maintained at 130° C. for 6 hours at which point the amount of reaction, determined by measurement of the free acidity, is 93%.

The product thus obtained is washed under agitation with 225 ml of water at 90° C. containing NaOH in an amount required for neutralization of the residual acidity and in the presence of 100 ml of isopropanol. The organic phase which is recovered after decantation is again washed twice with 225 ml of water at 90° C. and then dehydrated at 100° C. under reduced pressure, yielding a brownish wax having a drop point of 45° C.

EXAMPLE 11

Preparation of a mixture of compounds of general formula I wherein R represents a mixture of $C_{12}H_{25}$ and $C_{14}H_{29}$, R' represents $C_{21}H_{43}$ and X represents

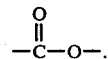

To 65.7 g (0.206 mole) of molten behenic acid there is added 0.34 g of powdered sodium methylate (6 meq). The temperature of the mixture is then raised to 130° C. under a current of nitrogen at which point there are added over a period of 35 minutes, 50.2 g (0.200 mole)

of a $C_{14}/C_{16}$ α-epoxide sold under the name α-Olefin Oxide 16.

The temperature of the reaction mixture is maintained at 130° C. for 7 hours. The amount of the reaction obtained under these conditions, determined by measurement of the free acidity, is 95%.

The product thus obtained is put into solution in 100 g of isopropanol and agitated with 100 ml of water at 90° C. containing a quantity of NaOH necessary to neutralize residual acid. The organic phase which is recovered after decantation is washed twice with 100 ml of water under the same conditions and then dehydrated with agitation at 90° C. under reduced pressure.

The product obtained is purified by recrystallization in acetone, yielding 66.5 g of a pale yellow powder having an end melting point of 60° C., a hydroxyl index of 1.44–1.46 meq/g and an ester index of 1.78 meq/g.

EXAMPLE 12

Preparation of a mixture of compounds of general formula I wherein R represents a mixture of $C_{12}H_{25}$ and $C_{14}H_{29}$, R' represents $C_{15}H_{31}$ and X represents

To 64.5 g (0.257 mole) of palmitic acid, there is added 0.44 g of powdered sodium methylate (0.007 mole). The reaction mass is then heated to 130° C. under a nitrogen atmosphere at which point there are added dropwise 59.5 g (0.25 mole) of a mixture of $C_{14}/C_{16}$ α-epoxides. The temperature of the reaction mixture is maintained at 130° C. for about 6 hours. The amount of reaction, determined by dosage of the acidity of the reaction mixture, is about 95%.

The product thus obtained is taken up in 100 ml of isopropanol and washed at 80° C. with 120 ml of boiling water in the presence of a quantity of NaOH necessary to neutralize the acidity.

The organic phase is decanted, washed twice with 120 ml of water and then dried by heating under reduced pressure.

The product obtained is a light yellow wax which is then recrystallized in 220 g of hexane. After recrystallization, the product is present in the form of a white powder having a melting point of 55°–60° C., a hydroxyl index of 1.90–1.92 meq/g, a saponification index of 2.05–2.09 meq/g and an acid index of 0.02 meq/g.

EXAMPLES OF COSMETIC COMPOSITIONS

EXAMPLE 13

A hygiene spray having the following composition is prepared:

| | |
|---|---|
| Product of Example 2 | 0.2 g |
| 2,4,4'-trichloro hydroxy diphenyl ether | 0.1 g |
| Hexylene glycol | 0.1 g |
| Perfume | 0.15 g |
| Propellant Freon 11/12, q.s.p. | 100 g |

EXAMPLE 14

A dye foundation having the following composition is prepared:

| | |
|---|---|
| Isopropyl lanolate | 4.0 g |
| Stearic acid | 2.6 g |
| Glycerol stearate (self-emulsifiable) | 5.0 g |
| Petrolatum oil | 6.0 g |
| Product of Example 5 | 14.0 g |
| Triethanolamine | 1.2 g |
| Sodium lauryl sulfate | 1.1 g |
| Bentonite | 2.5 g |
| Methyl para hydroxy benzoate | q.s. |
| Perfume | q.s. |
| Demineralized water, q.s.p. | 100 g |
| In addition: | |
| Titanium oxide | q.s. for the |
| Iron Oxide | tint and covering |
| Talc | power desired |

EXAMPLE 15

A lip rouge having the following composition is prepared:

| | |
|---|---|
| Ozokerite (fossile mineral wax) | 22 g |
| Liquid lanolin | 15 g |
| Ricin oil | 22 g |
| Oleyl alcohol | 10 g |
| Product of Example 5 | 30.75 |
| BHT (2,6-di-tert. butyl p-cresol) | 0.1 g |
| Methyl parahydroxy benzoate | 0.15 g |
| In addition: | 100 g |
| Dye | q.s. |
| Titanium oxide | according to |
| Nacreous agents | tint desired |

EXAMPLE 16

A dye foundation cream having the following composition is prepared:

| | |
|---|---|
| Polyethylene glycol stearate | 0.9 g |
| Glycerol stearate | 5 g |
| Petrolatum oil | 8 g |
| Product of Example 1 | 13 g |
| Isopropyl lanolate | 6 g |
| Cetyl alcohol | 2.2 g |
| Methyl para hydroxy benzoate | 0.3 g |
| Demineralized water, q.s.p. | 100 g |
| In addition: | |
| Titanium oxide | q.s. |
| Iron Oxide | according to |
| Kaolin | tint desired |

EXAMPLE 17

A dye foundation fluid having the following composition is prepared:

| | |
|---|---|
| Stearic acid | 4.6 g |
| Petrolatum oil | 5 g |
| Cetyl alcohol | 0.5 g |
| Product of Example 8 | 18 g |
| Triethanolamine | 1.8 g |
| Bentonite | 2 g |
| Methyl parahydroxy benzoate | 0.3 g |
| Demineralized water, q.s.p. | 100 g |
| In addition: | |
| Titanium oxide | q.s. |
| Kaolin and | according to |
| Iron oxides | tint desired |

EXAMPLE 18

An eyelid shadow having the following composition is prepared:

| | |
|---|---|
| Ozokerite | 35 g |
| Petrolatum | 6 g |
| Lanolin | 12 g |
| Product of Example 2 | 46.95 g |
| BHT | 0.05 g |
| | 100 g |

EXAMPLE 19

A cheek rouge having the following composition is prepared:

| | |
|---|---|
| Isopropyl stearate | 29 g |
| Product of Example 3 | 34 g |
| Glycerol monostearate | 30 g |
| Kaolin | 2 g |
| Titanium dioxide | 3.5 g |
| Iron oxide | 1.5 g |
| | 100 g |

EXAMPLE 20

A day cream for dry skin having the following composition is prepared:

| | |
|---|---|
| Stearyl ether polyoxyethylenated with 10 moles of ethylene oxide | 1.5 g |
| Cetyl ether polyoxyethylenated with 10 moles of ethylene oxide | 1.5 g |
| Cetyl alcohol | 1 g |
| Product of Example 5 | 20 g |
| Carbopol 934 | 0.3 g |
| Triethanolamine | 0.3 g |
| Sodium parahydroxy benzoate | 0.3 g |
| Water | 75.1 g |
| | 100 g |

Carbopol 934 is a carboxyvinyl polymer sold by Goodrich.

A similarly effective day cream is prepared by replacing in the above cream the product of Example 5 by the same quantity of the product of Example 8.

EXAMPLE 21

A day cream for dry skin having the following composition is prepared:

| | |
|---|---|
| Glycerol mmonostearate (self-emulsifiable) | 5.0 g |
| Product of Example 6 | 3.0 g |
| Petrolatum oil | 15.0 g |
| Purcellin oil | 3.0 g |
| Isopropyl palmitate | 5.0 g |
| Methyl para hydroxy benzoate | 0.3 g |
| Carbopol 940 | 0.4 g |
| Triethanolamine | 0.4 g |
| Demineralized sterile water, q.s.p. | 100 g |

Carbopol 940 is a carboxy vinyl polymer sold by Goodrich and Purcellin oil is a mixture of esters of fatty acids having branched chain.

A similarly effective day cream is prepared by replacing in the above cream the product of Example 6 by the same quantity of the product of Example 9.

EXAMPLE 22

A day cream for oily skin having the following composition is prepared:

| | |
|---|---|
| Emulgade F | 5.0 g |
| Cetyl alcohol | 1.0 g |
| Product of Example 3 | 10.0 g |
| Methyl parahydroxy benzoate | 0.3 g |
| Carbopol 940 | 0.4 g |
| Triethanolamine | 0.4 g |
| Demineralized sterile water, q.s.p. | 100 g |

Emulgade F is an emulsifying agent consisting of a mixture of cetyl alcohol, stearyl alcohol, sodium cetyl stearyl sulfate and nonionic emulsifiers.

A similarly effective day cream is prepared by replacing the product of Example 3 by the product of Example 4.

EXAMPLE 23

A lip rouge having the following composition is prepared:

| | |
|---|---|
| Microcrystalline wax | 18 g |
| Product of Example 12 | 12 g |
| Mineral oil | 20 g |
| Isopropyl lanolate | 10 g |
| Hydrogenated lanolin | 10 g |
| Acetylated lanolin | 20 g |
| Cetyl ricinoleate | 10 g |
| BHT (antioxidant) | 0.1 g |
| | 100.0 g |

EXAMPLE 24

A lip rouge having the following composition is prepared:

| | |
|---|---|
| Microcrystalline wax | 10 g |
| Candelilla wax | 4 g |
| Product of Example 11 | 10 g |
| Mineral oil | 16 g |
| Acetylated lanolin | 14 g |
| BHA (antioxidant) | 0.1 g |
| Lanolin | 20 g |
| Hydrogenated coconut oil | 10 g |
| Oleyl alcohol | 8 g |
| Ricin oil | 8 g |
| | 100.1 g |

To obtain a fatty lacquered lip rouge there is added to the above mixture 8–12% of a dye; to obtain a fatty nacreous lip rouge there is added 4–6% of dye plus a nacreous agent such as bismuth oxychloride—20–30% and titanium oxide—10–15%. In both cases perfume can also be added.

What is claimed is:

1. In a cosmetic composition for application to living human skin comprising a lip rouge, an eyelid shadow, a cream, a liquid dye foundation, a cheek rouge, or a hygiene spray and containing an excipient in an amount sufficient to impart to said cosmetic composition unctuousness, ease of application, and good spreadability on the skin, without an oily or greasy feel or touch, wherein the improvement comprises as said excipient at least one 1,2-alkanediol derivative selected from the group consisting of:

(1) a derivative having the formula

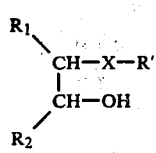

wherein X represents a member selected from the group consisting of oxygen and carbonyloxy of the formula

linked to R' through the free bond of the carbon atom of the carbonyloxy group, R' represents alkyl having 5-21 carbon atoms, said alkyl being the hydrocarbon residue of a member selected from the group consisting of R'OH and R'COOH wherein R' is defined above or where X represents

R' represents the hydrocarbon residue of lanolic acid, one of $R_1$ and $R_2$ represents linear alkyl having 8 to 16 carbon atoms and the other represents hydrogen; and (2) a mixture consisting of (1),
said excipient present in an amount sufficient to impart to said cosmetic composition unctuousness, ease of application and good spreadability on the skin, without an oily or greasy feel or touch.

2. The cosmetic composition of claim 1 wherein R' represents the hydrocarbon residue of a R'COOH acid selected from the group consisting of 2-ethyl butyric acid, 2-ethyl hexanoic acid, octanoic acid, 3,5,5-trimethyl hexanoic acid, decanoic acid, dodecanoic acid, neo-tridecanoic acid, tetradecanoic acid, hexadecanoic acid, isopalmitic acid, isostearic acid, octadecanoic acid, eicosanoic acid, docosanoic acid and lanolic acid.

3. The cosmetic composition of claim 1 wherein R' is the hydrocarbon residue of a R'OH alcohol selected from the group consisting of 2-ethyl hexanol, octanol, decanol, dodecanol, tetradecanol, hexadecanol, 2-hexyl decanol, 2-octyl decanol, octyl-octanol, isostearyl alcohol and 2-octyl dodecanol.

4. The cosmetic composition of claim 1 wherein one of $R_1$ and $R_2$ is selected from the group consisting of octyl, nonyl, decyl, undecyl, dodecyl, tridecyl, tetradecyl, pentadecyl and hexadecyl and the other is hydrogen.

5. The cosmetic composition of claim 1 wherein one of $R_1$ and $R_2$ represents alkyl having 9-12 carbon atoms and the other is hydrogen, R' represents the hydrocarbon residue of isostearyl alcohol and X represents oxygen.

6. The cosmetic composition of claim 1 wherein one of $R_1$ and $R_2$ represents tetradecyl and the other is hydrogen, R' represents 2-ethyl hexyl and X represents oxygen.

7. The cosmetic composition of claim 1 wherein one of $R_1$ and $R_2$ represents a mixture of dodecyl and tetradecyl and the other is hydrogen, R' represents 2-hexyl decyl and X represents oxygen.

8. The cosmetic composition of claim 1 wherein one of $R_1$ and $R_2$ represents alkyl having from 9 to 12 carbon atoms and the other is hydrogen, R' represents the hydrocarbon residue of 2-ethyl butyric acid and X represents

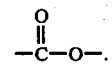

9. The cosmetic composition of claim 1 wherein one of $R_1$ and $R_2$ represents alkyl having from 13 to 16 carbon atoms and the other is hydrogen, R' represents the hydrocarbon residue of 2-ethyl hexanoic acid and X represents

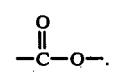

10. The cosmetic composition of claim 1 wherein one of $R_1$ and $R_2$ represents a mixture of dodecyl and tetradecyl and the other is hydrogen, R' represents the hydrocarbon residue of isostearic acid and X represents

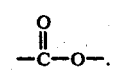

11. The cosmetic composition of claim 1 wherein one of $R_1$ and $R_2$ represents alkyl having from 9 to 12 carbon atoms and the other is hydrogen, R' represents the hydrocarbon residue of 3,5,5-trimethyl hexanoic acid and X represents

12. The cosmetic composition of claim 1 wherein one of $R_1$ and $R_2$ represents a mixture of dodecyl and tetradecyl and the other is hydrogen, R' represents the hydrocarbon residue of 2-ethyl hexanoic acid and X represents

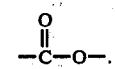

13. The cosmetic composition of claim 1 wherein one of $R_1$ and $R_2$ represents $C_{10}H_{21}$ and the other is hydrogen, R' represents the hydrocarbon residue of lanolic acid and X represents

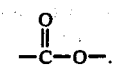

14. The cosmetic composition of claim 1 wherein one of $R_1$ and $R_2$ represents a mixture of $C_{12}H_{25}$ and $C_{14}H_{29}$ and the other is hydrogen, R' represents $C_{21}H_{43}$ and X represents

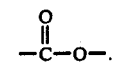

15. The cosmetic composition of claim 1 wherein one of $R_1$ and $R_2$ represents a mixture of $C_{12}H_{25}$ and $C_{14}H_{29}$ and the other is hydrogen, R' represents $C_{15}H_{31}$ and X represents

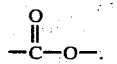

16. The cosmetic composition of claim 1 wherein one of $R_1$ and $R_2$ represents alkyl having from 13 to 16 carbon atoms, and the other is hydrogen, R' represents heptadecyl and X represents

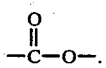

17. The cosmetic composition of claim 1 wherein said derivative is present in an amount ranging between 0.15 and 70 percent by weight of said composition.

18. The cosmetic composition of claim 1 wherein said derivative is present in an amount ranging between 0.2 and 50 percent by weight of said composition.

19. In a cosmetic composition for application to living human skin containing an excipient in an amount sufficient to impart to said cosmetic composition unctuousness, ease of application and good spreadability on the skin, without an oily or greasy feel or touch, wherein the improvement comprises as said excipient a 1,2-alkanediol derivative having the formula

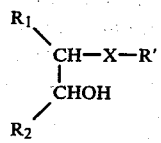

wherein X represents a carbonyloxy of the formula

linked to R' through the free bond of the carbon atom of the carbonyloxy group, one of $R_1$ and $R_2$ represents a mixture of $C_{12}H_{25}$ and $C_{14}H_{29}$ and the other is hydrogen, and R' represents $C_{15}H_{31}$.

20. The cosmetic composition of claim 19 comprising a lip rouge, an eyelid shadow, a cream, a liquid dye foundation, a cheek rouge or a hygiene spray.

21. In a cosmetic composition comprising a lip rouge, an eyelid shadow, a cream, a liquid dye foundation, a cheek rouge or a hygiene spray said cosmetic composition containing an excipient in an amount sufficient to impart to said cosmetic composition unctuousness, ease of application and good spreadability on the skin, without an oily or greasy feel or touch, wherein the improvement comprises as said excipient a 1,2-alkanediol derivative selected from the group consisting of (1) a derivative having the formula

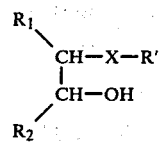

wherein X represents a carbonyloxy of the formula

linked to R' through the free bond of the carbon atom of the carbonyloxy group, R' represents the hydrocarbon residue R'COOH of 2-ethyl butyric acid, one of $R_1$ and $R_2$ represents alkyl having 9 to 12 carbon atoms and the other represents hydrogen; and (2) a mixture of (1).

22. In a cosmetic composition comprising a lip rouge, an eyelid shadow, a cream, a liquid dye foundation, a cheek rouge or a hygiene spray, said cosmetic composition containing an excipient in an amount sufficient to impart to said cosmetic composition unctuousness, ease of application and good spreadability on the skin, without an oily or greasy feel or touch, wherein the improvement comprises as said excipient a 1,2-alkanediol derivative selected from the group consisting of:

(1) a derivative having the formula

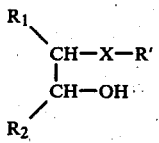

wherein X represents a carbonyloxy of the formula

linked to R' through the free bond of the carbon atom of the carbonyloxy group, R' represents the hydrocarbon residue R'COOH of 3,3,5-trimethyl hexanoic acid, one of $R_1$ and $R_2$ represents alkyl having 9 to 12 carbon atoms and the other represents hydrogen; and (2) a mixture of (1).

* * * * *